United States Patent [19]

Tamaru et al.

[11] Patent Number: 4,788,327
[45] Date of Patent: Nov. 29, 1988

[54] 4,4'-(PERFLUOROISOPROPYLIDENE)DICYCLOHEXANOL, DERIVATIVE THEREOF AND PROCESS FOR PREPARING THE SAME

[75] Inventors: Sinji Tamaru, Suita; Motonobu Kubo, Toyonaka, both of Japan

[73] Assignee: Daiken Industries, Ltd., Osaka, Japan

[21] Appl. No.: 157,871

[22] Filed: Feb. 19, 1988

[30] Foreign Application Priority Data

Feb. 20, 1987 [JP] Japan .................................. 62-38384

[51] Int. Cl.$^4$ ............................................. C07C 69/52
[52] U.S. Cl. .................................. 560/220; 560/231; 568/832; 260/410.5
[58] Field of Search ................ 560/220, 231; 568/832; 260/410.5

[56] References Cited

U.S. PATENT DOCUMENTS 3,162,615 12/1964 Bremmer .............................. 568/832

FOREIGN PATENT DOCUMENTS 478018 10/1951 Canada ................................. 568/832

*Primary Examiner*—Paul J. Killos
*Attorney, Agent, or Firm*—Armstrong, Nikaido, Marmelstein & Kubovcik

[57] ABSTRACT

4,4'-(Perfluoroisopropylidene)dicyclohexanol or its organic acid ester of the formula

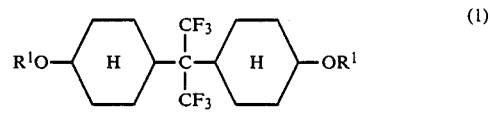

wherein R' is hydrogen atom or acyl group having 1 to 10 carbon atoms, is useful as a starting material of a curable resin, cross-linking agent or the like.

5 Claims, No Drawings

4,4'-(PERFLUOROISOPROPYLIDENE)DICYCLOHEXANOL, DERIVATIVE THEREOF AND PROCESS FOR PREPARING THE SAME

The present invention relates to 4,4'-(perfluoroisopropylidene)dicyclohexanol, derivative thereof and process for preparing the same.

Conventionally, various diols and their di(meth)acrylates are used as a starting material of a curable resin, cross-linking agent or the like. For example, 4,4'-(perfluoroisopropylidene)diphenol (hereinafter referred to as "bisphenol AF") is used as a monomer or a starting material therefor of an epoxy resin, polyacrylate resin, polyurethane resin or urethane (meth)acrylate resin, cross-linking agent for rubber or the like. Epoxy resin or polyurethane resin using bisphenol AF has an excellent heat resistance but is insufficient in weather resistance.

Further, a resin obtained by using bisphenol AF di(meth)acrylate or 4,4'-dihydroxydiphenylsulfone (bisphenol S) di(meth)acrylate is excellent in heat resistance but is inferior in weather resistance.

An object of the invention is to provide a novel fluorine-containing derivative and a process thereof, the derivative being useful as a component of an acrylic resin which is excellent in both of heat resistance and weather resistance.

The above and other objects of the invention will become apparent from the following description.

The present invention provides a 4,4'-(perfluoroisopropylidene)dicyclohexanol or its organic acid ester of the formula

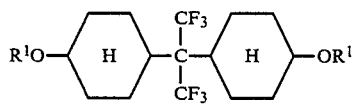

wherein $R^1$ is hydrogen atom or acyl group having 1 to 10 carbon atoms.

In the present invention, the compound of the formula (1) wherein $R^1$ is hydrogen atom, namely 4,4'-(perfluoroisopropylidene)dicyclohexanol can be prepared, for example, by reacting bisphenol AF with hydrogen. The reaction is conducted preferably in a solvent such as methanol, ethanol, n-propanol, isopropanol and n-butanol. Hydrogen is used preferably at a pressure of about 1 to 250 kg/cm$^2$G, more preferably of about 10 to 100 kg/cm$^2$G. It is preferable to use a catalyst such as elemental ruthenium, palladium, platinum or rhodium, oxides thereof and Raney nickel. The elemental metal is preferably used as supported on a carrier such as carbon, alumina and zeolite. Especially preferable is ruthenium. The metal is supported preferably in an amount of about 0.01 to 30% by weight based on the carrier. The catalyst is used preferably in an amount of about 0.001 to 20% by weight in term of metal based on the starting material. The preferred reaction temperature is about 20° to 250° C., more preferably about 100° to 200° C. The desired 4,4'-(perfluoroisopropylidene)dicyclohexanol can be isolated and purified by a known method such as filtration, distillation, recrystallization and column chromatography.

The compound of the formula (1) in which $R^1$ is acyl group, namely an organic acid ester of 4,4'-(perfluoroisopropylidene)dicyclohexanol can be obtained by reacting 4,4'-(perfluoroisopropylidene)dicyclohexanol with an organic acid or derivative thereof. Examples of the organic acids are acrylic acid, methacrylic acid, vinylacetic acid, formic acid, acetic acid, propionic acid, n-butyric acid, n-valerianic acid and caproic acid. Typical examples of reactive derivatives are acid halides such as acrylic acid chloride and methacrylic acid chloride. The organic acid or reactive derivative thereof is reacted in an amount of about 2 to 20 moles per mole of 4,4'-(perfluoroisopropylidene)dicyclohexanol.

The reaction is conducted preferably in a solvent in the presence of a base. The solvent include ethyl ether, tetrahydrofuran, dioxane, acetone, methyl ethyl ketone, chloroform, benzene and the like. Examples of bases are NaOH, metal magnesium, triethylamine, dimethylaniline, pyridine and quinoline. The base is used preferably in an amount of about 1 to 10 moles per mole of the organic acid or reactive derivative thereof. The preferred reaction temperature is about 0° to 100° C. The resulting organic ester of 4,4'-(perfluoroisopropylidene)dicyclohexanol can be isolated and purified by a known method such as filtration, distillation, recrystallization and column chromatography.

Among these organic acid esters, acrylic acid esters and methacrylic acid esters are those represented by the formula (1) wherein $R^1$ is CH$_2$=C(X)CO—, X is hydrogen atom or methyl group. These (meth)acrylic acid esters are useful as a component of an acrylic resin which are excellent in both of heat resistance and weather resistance. Organic acid esters other than the above esters are useful as a material for preparing a polyester through a transesterification, for example, with a dibasic acid.

The present invention will be described in detail by showing examples.

EXAMPLE 1

Into a stainless steel autoclave were placed 500 g of 4,4'-(perfluoroisopropylidene)diphenol, 100 ml of isopropanol and 2 g of 5% ruthenium-carbon. The mixture was maintained at a temperature of 130° C. and a hydrogen pressure of 50 kg/cm$^2$G for 40 minutes and then at 160° to 170° C. and a hydrogen pressure of 60 to 70 kg/cm$^2$G for 40 minutes. After cooled to room temperature, the catalyst is filtered off and isopropanol was removed at a reduced pressure. The residue was recrystallized from toluene to obtain 290 g of 4,4'-(perfluoroisopropylidene)dicyclohexanol in the form of white solid.

Elementary analysis (C$_{15}$H$_{22}$F$_6$O$_2$) Theor.; C 51.72%, H 6.37%, F 32.73%, Found; C 51.21%, H 6.51%, F 31.95%.

$^1$H-NMR (in acetone-d$_6$, TMS standard, δppm)

3.5, m, 2H 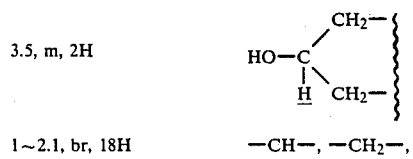

1~2.1, br, 18H    —CH—, —CH$_2$—,

REFERENCE EXAMPLE 1

In 300 g of acetone were dissolved 46.2 g of isophoronediisocyanate, 70.3 g of 4,4'-(perfluoroisopropylidene)dicyclohexanol and 0.8 g of di-n-butyltin dilaurate. The mixture was reacted at 54° to 56° C. for 15 hours with stirring while introducing dry nitrogen. To the mixture were added 10 g of 2-hydroxyethyl acrylate, 0.4 g of di-n-butyltin dilaurate and 0.1 g of hydroquinone monomethyl ether and the mixture was reacted at 54° to 56° C. for 16 hours. A few drops of the reaction mixture were placed on KBr plate. The plate was dried and subjected to infrared absorption spectrum analysis to find an absorption based on isocyanate group (2250 cm$^{-1}$) disappeared. The reaction mixture was poured into a large excess amount of hexane and the resulting precipitates were filtered, dried and pulverized to obtain 114 g of urethane acrylate in the form of white powder.

The above urethane acrylate (30 g) was mixed with 30 g of tetrahydrofurfuryl acrylate and 0.6 g of benzoyl peroxide and the mixture was degassed at a reduced pressure. The resulting viscous liquid was poured into a polytetrafluoroethylene mold and heated in an oil-bath at 65° C. for 3 hours, 80° C., for 3 hours and 100° C., for 10 hours to prepare a casting plate having a thickness of 3 mm.

REFERENCE EXAMPLE 2

A casting plate was prepared in the same manner as in Reference Example 1 except that 68.0 g of 4,4'-(perfluoroisopropylidene)diphenyl [bisphenol AF] was used in place of 4,4'-(perfluoroisopropylidene)dicyclohexanol.

TEST EXAMPLE 1

The casting plates of Reference Examples 1 and 2 were checked for weight loss commencing temperature and change in appearance after accelerated weather test (sunshine weather-ometer, 200 hours). The results were given in Table 1.

TABLE 1

|  | Ref. Ex. 1 | Ref. Ex. 2 |
| --- | --- | --- |
| Weight loss commencing temperature (°C.) | 207 | 208 |
| Accelerated weather test (change in appearance) | No change | change to yellow |

EXAMPLE 2

Into a reaction vessel equipped with a stirrer, thermometer and dropping funnel were placed 0.3 mole (104.4 g) of 4,4'-(perfluoroisopropylidene)dicyclohexanol, 1 mole (101.2 g) of triethylamine and 700 ml of tetrahydrofuran. To the mixture was added dropwise 1 mole (104.5 g) of methacryloyl chloride while cooling the mixture with ice. The mixture was maintained at a temperature below 20° C. for 8 hours with stirring. The reaction mixture was poured into a large excess amount of water and the resulting precipitates were recovered and washed with methanol to obtain 69 g of 4,4'-(perfluoroisopropylidene)dicyclohexanol dimethacrylate in the form of white solid.

Elementary analysis ($C_{23}H_{30}F_6O_4$): Theor.; C, 57.02%, H, 6.24%, F, 23.53%, Found; C, 57.32%, H, 5.99%, F, 23.11%.

$^1$H-NMR (in CDCl$_3$, TMS standard, δppm)

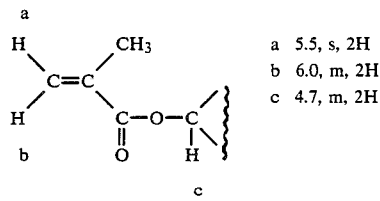

a 5.5, s, 2H
b 6.0, m, 2H
c 4.7, m, 2H

—CH—, —CH$_2$—, —CH$_3$ 1.2~2.3, br, 24H.

EXAMPLE 3

A 42 g-quantity of 4,4'-(perfluoroisopropylidene)dicyclohexanol diacrylate was prepared in the same manner as in Example 2 except that 1 mole (90.5 g) of acryloyl chloride was used in place of methacryloyl chloride.

Elementary analysis ($C_{21}H_{26}F_6O_4$): Theor.; C, 55.26%, H, 5.74%, F, 24.98%, Found; C, 54.88%, H, 5.71%, F, 24.32%.

$^1$H-NMR (in CDCl$_3$, TMS standard, δppm)

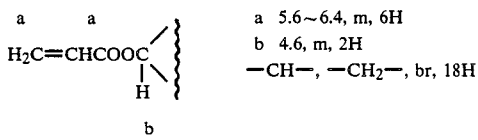

a 5.6~6.4, m, 6H
b 4.6, m, 2H
—CH—, —CH$_2$—, br, 18H

COMPARISON EXAMPLE 1

Bisphenol AF dimethacrylate (72 g) was obtained in the same manner as in Example 2 except that 0.3 mole (100.8 g) of 4,4'-(perfluoroisopropylidene)diphenol [bisphenol AF] was used in place of 4,4'-(perfluoroisopropylidene)dicyclohexanol.

REFERENCE EXAMPLES 3 AND 4

In 100 g of tetrahydrofurfuryl acrylate was dissolved each of dimethacrylate (20 g) of Example 2 and Comparison Example 1. To the solution was added 1 g of benzoyl peroxide and the mixture was poured into a polytetrafluoroethylene mold and heated in an oil-bath at 65° C. for 3 hours, 80° C. for 3 hours and 100° C. for 10 hours to prepare a casting plate each having a thickness of 3 mm.

TEST EXAMPLE 2

The casting plates of Reference Examples 3 and 4 were checked for weight loss commencing temperature and change in appearance after accelerated weather test (sunshine weather-ometer, 200 hours). The results were given in Table 2.

TABLE 2

|  | Ref. Ex. 3 | Ref. Ex. 4 |
| --- | --- | --- |
| Weight loss commencing temperature (°C.) | 202 | 204 |
| Accelerated weather test (change in appearance) | No change | change to yellow |

We claim:
1. 4,4'-(Perfluoroisopropylidene)dicyclohexanol or its organic acid ester of the formula

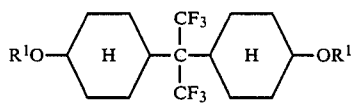

wherein $R^1$ is hydrogen atom or acyl group having 1 to 10 carbon atoms.

2. An organic acid ester as defined in claim 1 wherein $R^1$ is $CH_2=C(X)CO-$, X is hydrogen atom or methyl group.

3. A process for preparing 4,4'-(perfluoroisopropylidene)dicyclohexanol of the formula

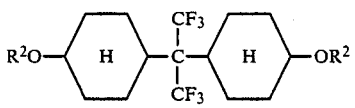

wherein $R^2$ is hydrogen atom which comprises reacting hydrogen with 4,4'-(perfluoropropylidene)diphenol.

4. A process for preparing an organic acid ester of 4,4'-(perfluoroisopropylidene)dicyclohexanol of the formula

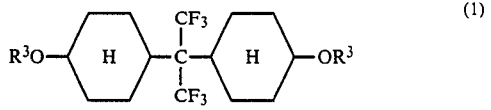

wherein $R^3$ is acyl group which comprises reacting an organic acid or reactive derivative thereof with 4,4'-(perfluoroisopropylidene)dicyclohexanol.

5. A process for preparing an organic acid ester as defined in claim 4 wherein the organic acid or reactive derivative thereof is acrylic acid, methacrylic acid or reactive derivative thereof and $R^3$ is $CH_2=C(X)CO-$, X is hydrogen atom or methyl group.

* * * * *